United States Patent [19]

Berg et al.

[11] Patent Number: 4,793,901

[45] Date of Patent: Dec. 27, 1988

[54] SEPARATION OF 2-PENTANONE FROM FORMIC ACID BY EXTRACTIVE DISTILLATION

[75] Inventors: Lloyd Berg; Rudolph J. Szabados, both of Bozeman, Mont.

[73] Assignee: Hoechst Celanese Chemical Co., Pampa, Tex.

[21] Appl. No.: 180,129

[22] Filed: Apr. 11, 1988

[51] Int. Cl.$^4$ .................. B01D 3/40; C07C 45/83; C07C 53/02
[52] U.S. Cl. ........................... 203/51; 203/56; 203/57; 203/60; 203/61; 203/62; 203/63; 203/64; 203/65; 562/609; 568/410
[58] Field of Search .................. 203/51, 57, 56, 60, 203/61, 62, 63, 64, 65; 568/410; 562/609

[56] References Cited

U.S. PATENT DOCUMENTS

| | | | |
|---|---|---|---|
| 2,010,384 | 8/1935 | van Melsen | 568/410 |
| 2,586,929 | 2/1952 | Fleming et al. | 568/410 |
| 2,954,392 | 9/1960 | Rylander | 568/410 |
| 3,013,954 | 12/1961 | Pacoud et al. | 203/62 |
| 3,228,985 | 1/1966 | Carpenter et al. | 568/410 |
| 3,265,592 | 8/1966 | van der Weel | 568/410 |
| 4,459,178 | 7/1984 | Berg | 203/51 |

Primary Examiner—Wilbur Bascomb

[57] ABSTRACT

2-Pentanone cannot be completely removed from 2-pentanone and formic acid mixtures by distillation because of the presence of the maximum azeotrope. 2-Pentanone can be readily removed from 2-pentanone formic acid mixtures by extractive distillation in which the extractive agent is dimethylsulfoxide, either alone or mixed with certain high boiling organic compounds. Examples of effective agents are dimethylsulfoxide; DMSO and octanoic acid; DMSO, hexanoic acid and isophorone.

2 Claims, No Drawings

SEPARATION OF 2-PENTANONE FROM FORMIC ACID BY EXTRACTIVE DISTILLATION

FIELD OF THE INVENTION

This invention relates to a method for separating formic acid from 2-pentanone using certain higher boiling liquids as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, and liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in the direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Formic acid, B.P.=100.8° C., and 2-pentanone, B.P.=102.4° C. form a maximum azeotrope boiling at 105.5° C. and containing 32 wt.% formic acid. When these two are found together in mixtures, either alone or with other liquids, distillation will only produce the azeotrope, never pure formic acid or 2-pentanone. Thus any liquid mixture containing these two will on distillation produce the azeotrope. Extractive distillation would be an attractive method of effecting the separation of formic acid from 2-pentanone if agents can be found that (1) will break the formic acid-2-pentanone azeotrope and (2) are easy to recover from the formic acid, that is, form no azeotrope with formic acid and boil sufficiently above formic acid to make the separation by rectification possible with only a few theoretical plates.

Extractive distillation typically requires the addition of an equal amount to twice as much extractive agent as the 2-pentanone and formic acid on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The object of this invention is to provide a process or method of extractive distillation that will enhance the relative volatility of 2-pentanone to formic acid in their separation in a rectification column. It is a further object of this invention to identify suitable extractive distillation agents which will eliminate the 2-pentanone-formic acid azeotrope and make possible the production of pure 2-pentanone and formic acid by rectification. It is a further object of this invention to identify organic compounds which are stable, can be separated from formic acid by rectification with relatively few plates and can be recycled to the extractive distillation column and reused with little decomposition.

SUMMARY OF THE INVENTION

The objects of the invention are provided by a process for separating 2-pentanone from formic acid which entails the use of certain oxygenated or sulfur containing organic compounds as the agent in extractive distillation.

DETAILED DESCRIPTION OF THE INVENTION

We have discovered that dimethylsulfoxide (DMSO), either alone or admixed with other high boiling organic compounds, will effectively negate the 2-pentanone-formic acid maximum azeotrope and permit the separation of 2-pentanone from formic acid by rectification when employed as the agent in extractive distillation. Table 1 lists DMSO and its mixtures and the approximate proportions that we have found to be effective.

TABLE 1

Extractive Distillation Agents Which Are Effective In Breaking The 2-Pentanone - Formic Acid Azeotrope

| Compounds | Ratios | | Relative Volatility | |
|---|---|---|---|---|
| Dimethylsulfoxide (DMSO) | 1 | 6/5 | 9.8 | 10.2 |
| DMSO, Hexanoic acid | $(1/2)^2$ | $(3/5)^2$ | 4.8 | 1.5 |
| DMSO, Heptanoic acid | " | " | 4.4 | 5.0 |
| DMSO, Octanoic acid | " | " | 6.3 | 5.6 |
| DMSO, Pelargonic acid | " | " | 4.4 | 4.8 |
| DMSO, Decanoic acid | " | " | 4.7 | 4.5 |
| DMSO, Neodecanoic acid | " | " | 4.2 | 3.8 |

TABLE 1-continued

Extractive Distillation Agents Which Are Effective In Breaking The 2-Pentanone - Formic Acid Azeotrope

| Compounds | Ratios | | Relative Volatility | |
|---|---|---|---|---|
| DMSO, Cinnamic acid | " | " | 3.3 | 3.3 |
| DMSO, Salicylic acid | " | " | 3.2 | 2.9 |
| DMSO, Acetyl salicylic acid | " | " | 4.1 | 2.8 |
| DMSO, Adipic acid | " | " | 2.6 | 2.7 |
| DMSO, Sebacic acid | " | " | 3.7 | 3.1 |
| DMSO, Azelaic acid | " | " | 3.8 | 3.4 |
| DMSO, Dodecanedioic acid | " | " | 3.7 | 3.3 |
| DMSO, Itaconic acid | " | " | 2.9 | 3.9 |
| DMSO, p-tert. Butyl benzoic acid | " | " | 2.0 | 2.0 |
| DMSO, o-Toluic acid | " | " | 2.5 | 2.3 |
| DMSO, m-Toluic acid | " | " | 2.8 | 3.2 |
| DMSO, p-Toluic acid | " | " | 2.8 | 2.5 |
| DMSO, p-Hydroxybenzoic acid | " | " | 1.9 | 3.2 |
| DMSO, Malic acid | " | " | 7.1 | 6.1 |
| DMSO, Glutaric acid | " | " | 2.5 | 2.7 |
| DMSO, Neopentanoic acid | " | " | 4.1 | 2.9 |
| DMSO, 2-Benzoylbenzoic acid | " | " | 3.2 | 6.8 |
| DMSO, Anisole | " | " | 5.0 | 5.4 |
| DMSO, Hexanoic acid, Isophorone | $(1/3)^3$ | $(2/5)^3$ | 5.0 | 5.0 |
| DMSO, Heptanoic acid, Butyl benzoate | " | " | 3.6 | 3.4 |
| DMSO, Pelargonic acid, Methyl benzoate | " | " | 3.4 | 3.6 |
| DMSO, Decanoic acid, Acetophenone | " | " | 4.2 | 3.8 |
| DMSO, Neodecanoic acid, Ethyl benzoate | " | " | 3.8 | 3.8 |
| DMSO, Cinnamic acid, Benzyl benzoate | " | " | 2.1 | 1.9 |
| DMSO, Salicylic acid, Adiponitrile | " | " | 2.4 | 2.9 |
| DMSO, Acetyl salicylic acid, 2,4-Pentanedione | " | " | 3.2 | 2.4 |
| DMSO, Glutaric acid, Diethylene glycol diethyl ether | " | " | 4.2 | 4.2 |
| DMSO, Adipic acid, Diethylene glycol dimethyl ether | " | " | 2.9 | 2.9 |
| DMSO, Sebacic acid, Butyl ether | " | " | 2.7 | 2.6 |
| DMSO, Azelaic acid, Benzyl ether | " | " | 2.4 | 2.3 |
| DMSO, Dodecanedioic acid, Methyl benzoate | " | " | 2.2 | 2.6 |
| DMSO, Itaconic acid, Methyl salicylate | " | " | 1.9 | 2.5 |
| DMSO, p-tert. Butyl benzoic acid, Dipropylene glycol dibenzoate | " | " | 1.7 | 1.8 |
| DMSO, Glutaric acid, Anisole | " | " | 2.7 | 1.7 |
| DMSO, o-Toluic acid, Phorone | " | " | 1.7 | 1.5 |
| DMSO, m-Toluic acid, Acetonylacetone | " | " | 2.3 | 2.1 |
| DMSO, p-Toluic acid, Ethylene glycol diacetate | " | " | 1.7 | 1.5 |
| DMSO, p-Hydroxybenzoic acid, Glycerol triacetate | " | " | 2.0 | 1.9 |
| DMSO, Malic acid, Diethylene glycol diethyl ether | " | " | 2.1 | 2.6 |
| DMSO, Glutaric acid, Benzophenone | " | " | 2.1 | 1.9 |
| DMSO, Heptanoic acid, Diethylene glycol dimethyl ether | " | " | 4.4 | 5.7 |
| DMSO, Heptanoic acid, Anisole | " | " | 3.2 | 2.5 |
| DMSO, Pelargonic acid, Diethylene glycol dimethyl ether | " | " | 4.9 | 2.7 |
| DMSO, Neopentanoic acid, Ethyl acetoacetate | " | " | 1.3 | 3.3 |
| DMSO, 2-Benzoylbenzoic acid, Diethylene glycol diethyl ether | " | " | 1.8 | 6.1 |

TABLE 2

Data From Run Made In Rectification Column.

| Agent | Column | Time, hrs. | Weight % 2-Pentanone | Weight % Formic acid | Relative Volatility |
|---|---|---|---|---|---|
| 33% DMSO, | Overhead | ½ | 95.8 | 4.2 | 2.0 |
| 33% Pelargonic acid, | Bottoms | | 50.6 | 49.4 | |
| 33% Methyl benzoate | Overhead | 1 | 98.7 | 1.3 | 2.57 |
| | Bottoms | | 52.5 | 47.5 | |
| | Overhead | 2 | 97.8 | 2.2 | 2.15 |
| | Bottoms | | 59.1 | 40.9 | |

The data in Table 1 was obtained in a vapor-liquid equilibrium still. In case, the starting material was the 2-pentanone-formic acid azeotrope. The ratios are the parts by weight of extractive agent used per part of 2-pentanone-formic acid azeotrope. The relative volatilities are listed for each of the two ratios employed. The compounds which are effective when used in mixtures with DMSO are hexanoic acid, heptanoic acid, octanoic acid, pelargonic acid, decanoic acid, neodecanoic acid, benzoic acid, salicylic acid, cinnamic acid, o-toluic acid, m-toluic acid, p-toluic acid, o-hydroxybenzoic acid, p-tert. butyl benzoic acid, azelaic acid, isophorone, methyl benzoate, ethyl benzoate, acetophenone, butyl benzoate, adiponitrile, diethylene glycol diethyl ether, dipropylene glycol dibenzoate, ethylene glycol diacetate, glycerol triacetate, benzyl ether, glutaric acid and anisole.

The two relative volatilities shown in Table 1 correspond to the two different ratios investigated. For example, in Table 1, one part of DMSO mixed with one part of the 2-pentanone-formic acid azeotrope gives a relative volatility of 9.8; with 6/5 parts of DMSO, the relative volatility is 10.2. One half part of DMSO mixed with one half part of octanoic acid with one part of the 2-pentanone-formic acid azeotrope gives a relative volatility of 6.3; 3/5 parts of DMSO plus 3/5 parts of octanoic acid give 5.6. One third part of DMSO plus ⅓ part of hexanoic acid plus ⅓ part of isophorone with one part of the 2-pentanone-formic acid azeotrope gives a relative volatility of 5.0; with 2/5 parts, these three give a relative volatility of 5.0. In every example in Table 1, the starting material is the 2-pentanone-formic acid azeotrope which possesses a relative volatility of 1.00.

One of the mixtures, DMSO, pelargonic acid and methyl benzoate, listed in Table 1 and whose relative volatility had been determined in the vapor-liquid equilibrium still, was then evaluated in a glass perforated plate rectification column possessing 4.5 theoretical plates and the results listed in Table 2. The data in Table 2 was obtained in the following manner. The charge was 250 grams of the 2-pentanone-formic acid azeotrope and after a half hour of operation in the 4.5 theoretical plate column to establish equilibrium, 33% DMSO, 33% pelargonic acid and 33% methyl benzoate at 95° C. and 20 ml/min. was pumped in. The rectification was continued with sampling of the overhead and bottoms after one half hour. The analysis is shown in Table 2 and was 95.% 2-pentanone, 4.2% formic acid in the overhead and 50.6% 2-pentanone, 49.4% formic acid in the bottoms which gives a relative volatility of 2.0 of 2-pentanone to formic acid. After one hour of continuous operation, the overhead was 98.7% 2-pentanone, 1.3% formic acid and the bottoms was 52.5% 2-pentanone, 47.5% formic acid which is a relative volatility of 2.57. After two hours of continuous operation, the overhead was 97.8% 2-pentanone, 2.2% formic acid and the bottoms was 59.1% 2-pentanone, 40.9% formic acid which is a relative volatility of 2.15. This proves that the extractive distillation agent is negating the azeotrope and makes the rectification proceed as if the azeotrope no longer existed and brings out the pure 2-pentanone as overhead.

THE USEFULNESS OF THE INVENTION

The usefulness or utility of this invention can be demonstrated by referring to the data presented in Tables 1 and 2. All of the successful extractive distillation agents show that 2-pentanone and formic acid can be separated from their maximum azeotrope by means of distillation in a rectification column and that the ease of separation as measured by relative volatility is considerable. Without these extractive distillation agents, no improvement about the azeotrope composition will occur in the rectification column. The data also show that the most attractive agents will operate at a boilup rate low enough to make this a useful and efficient method of recovering high purity 2-pentanone and formic acid from any mixture of these two including the maximum azeotrope. The stability of the compounds used and the boiling point difference in such that complete recovery and recycle is obtainable by a simple distillation and the amount required for make-up is small.

WORKING EXAMPLES

Example 1

Fifty grams of the 2-pentanone-formic acid azeotrope and 50 grams of dimethylsulfoxide (DMSO) were charged to a vapor-liquid equilibrium still and refluxed for eleven hours. Analysis indicated a vapor composition of 90.5% 2-pentanone, 9.5% formic acid, a liquid composition of 49.2% 2-pentanone, 50.8% formic acid which is a relative volatility of 9.8. Ten grams of DMSO were added and refluxing continued for another eleven hours. Analysis indicated a vapor composition of 93.2% 2-pentanone, 6.8% formic acid, a liquid composition of 57.4% 2-pentanone, 42.6% formic acid which is a relative volatility of 10.2.

Example 2

Fifty grams of the 2-pentanone-formic acid azeotrope, 25 grams of DMSO and 25 grams of octanoic acid were charged to the vapor-liquid equilibrium still and refluxed for 12 hours. Analysis indicated a vapor composition of 83.3% 2-pentanone, 16.7% formic acid and a liquid composition of 44.4% 2-pentanone, 55.6% formic acid which is a relative volatility of 6.3. Five grams of DMSO and five grams of octanoic acid were added and refluxing continued for another 12 hours. Analysis indicated a vapor composition of 80.9% 2-pentanone, 19.1% formic acid and a liquid composition of 43.1% 2-pentanone, 56.9% formic acid which is a relative volatility of 5.6.

Example 3

Fifty grams of the 2-pentanone-formic acid azeotrope, 17 grams of DMSO, 17 grams of hexanoic acid and 17 grams of isophorone were charged to the vapor-liquid equilibrium still and refluxed for 13 hours. Analysis indicated a vapor composition of 77.5% 2-pentanone, 22.5% formic acid and a liquid composition of 40.7% 2-pentanone, 59.3% formic acid which is relative volatility of 5.0. Three grams each of DMSO, hexanoic acid and isophorone were added and refuxing continued for another eleven hours. Analysis indicated a vapor composition of 77.5% 2-pentanone, 22.5% formic acid and a liquid composition of 40.8% 2-pentanone, 59.2% formic acid which is a relative volatility of 5.0.

Example 4

A glass perforated plate rectification column was calibrated with ethylbenzene and p-xylene which possesses a relative volatility of 1.06 and found to have 4.5 theoretical plates. A solution comprising 250 grams of the 2-pentanone-formic acid azeotrope was placed in the stillpot and heated. When refluxing began, an extractive agent comprising 33% DMSO, 33% pelargonic acid and 33% methyl benzoate was pumped into the column at a rate of 20 ml/min. The temperature of the extractive agent as it entered the column was 95° C. After establishing the feed rate of the extractive agent, the heat input to the 2-pentanone-formic acid in the stillpot was adjusted to give a total reflux rate of 10-20 ml/min. After one half hour of operation, the overhead and bottoms samples of approximately two ml. were collected and analysed by gas chromatography. The overhead analysis was 95.8% 2-pentanone, 4.2% formic acid. The bottoms analysis was 50.6% 2-pentanone, 49.4% formic acid. Using these compositions in the Fenske equation, with the number of theoretical plates in the column being 4.5, gave an average relative volatility of 2.0 for each theoretical plate. After one hour of continuous operation, the overhead was 98.7% 2-pentanone, 1.3% formic acid and the bottoms was 52.5% 2-pentanone, 47.5% formic acid which is a relative volatility of 2.57. After two hours of continuous operation, the overhead was 97.8% 2-pentanone, 2.2% formic acid and the bottoms was 59.1% 2-pentanone, 40.9% formic acid which is a relative volatility of 2.15.

We claim:

1. A method for recovering 2-pentanone from mixtures of 2-pentanone and formic acid which comprises distilling a mixture of 2-pentanone and formic acid in a rectification column in the presence of about one part of an extractive agent per part of 2-pentanone-formic acid mixture, recovering 2-pentanone as overhead product and obtaining the formic acid and the extractive agent from the stillpot, wherein said extractive agent comprises dimethylsulfoxide.

2. The method of claim 1 in which the extractive agent comprises dimethylsulfoxide and at least one member from the group consisting of hexanoic acid, heptanoic acid, octanoic acid, pelargonic acid, decanoic acid, neodecanoic acid, cinnamic acid, salicylic acid, acetyl salicylic acid, glutaric acid, adipic acid, sebacic acid, azelaic acid, itaconic acid, dodecanedioic acid, p-tert. butyl benzoic acid, o-toluic acid, m-toluic acid, p-toluic acid, p-hydroxybenzoic acid, malic acid, neopentanoic acid, 2-benzoylbenzoic acid, anisole, isophorone, butyl benzoate, methyl benzoate, ethyl benzoate, benzyl benzoate, butyl ether, acetophenone, adiponitrile, 2,4-pentanedione, diethylene glycol diethyl ether, diethylene glycol dimethyl ether, benzyl ether, methyl salicylate, dipropylene glycol dibenzoate, phorone, acetonylacetone, ethylene glycol diacetate, glycerol triacetate, benzophenone and ethyl acetoacetate.

* * * * *